United States Patent [19]
Sobel

[11] 3,937,743
[45] Feb. 10, 1976

[54] MAINTAINING HF SOLUBILITY IN ALKYLATION ISOBUTANE RECYCLE

[75] Inventor: Jay E. Sobel, Highland Park, Ill.

[73] Assignee: Universal Oil Products Company, Des Plaines, Ill.

[22] Filed: Feb. 18, 1975

[21] Appl. No.: 550,897

[52] U.S. Cl. .......................................... 260/683.48
[51] Int. Cl.² .............................................. C07C 3/54
[58] Field of Search .................. 260/683.48, 683.49

[56] References Cited
UNITED STATES PATENTS

| | | | |
|---|---|---|---|
| 3,211,536 | 10/1965 | VanPool | 260/683.48 |
| 3,322,850 | 5/1967 | Waldby et al. | 260/683.48 |
| 3,346,660 | 10/1967 | Hutson, Jr. et al. | 260/683.49 |
| 3,763,022 | 10/1973 | Chapman | 260/683.48 |
| 3,775,510 | 11/1973 | Hutson, Jr. et al. | 260/683.48 |
| 3,796,769 | 3/1974 | Ward | 260/683.48 |
| 3,845,158 | 10/1974 | Sobel | 260/683.49 |

Primary Examiner—Delbert E. Gantz
Assistant Examiner—G. J. Crasanakis
Attorney, Agent, or Firm—James R. Hoatson, Jr.; Thomas K. McBride; William H. Page, II

[57] ABSTRACT

In an HF alkylation process it has been found that combining olefin-acting reactant with a recycle stream including isobutane and HF upstream of an alkylation reaction zone is not harmful to alkylate product quality except when the HF is in a free state, i.e., the HF concentration is above the HF solubility level of the recycle stream. Soluble HF in the recycle stream is not harmful to alkylate product quality, therefore, in an embodiment, the overhead vapor stream of an isobutane stripper is condensed, cooled to a separation temperature, and separated into an HF phase and a hydrocarbon phase, a portion of which is withdrawn as an acid saturated recycle stream including isobutane and entrained acid, and heated to a temperature sufficient to place in solution the entrained acid prior to combination of the acid saturated recycle stream with the olefin-acting reactants.

6 Claims, 1 Drawing Figure

U.S. Patent  Feb. 10, 1976  3,937,743
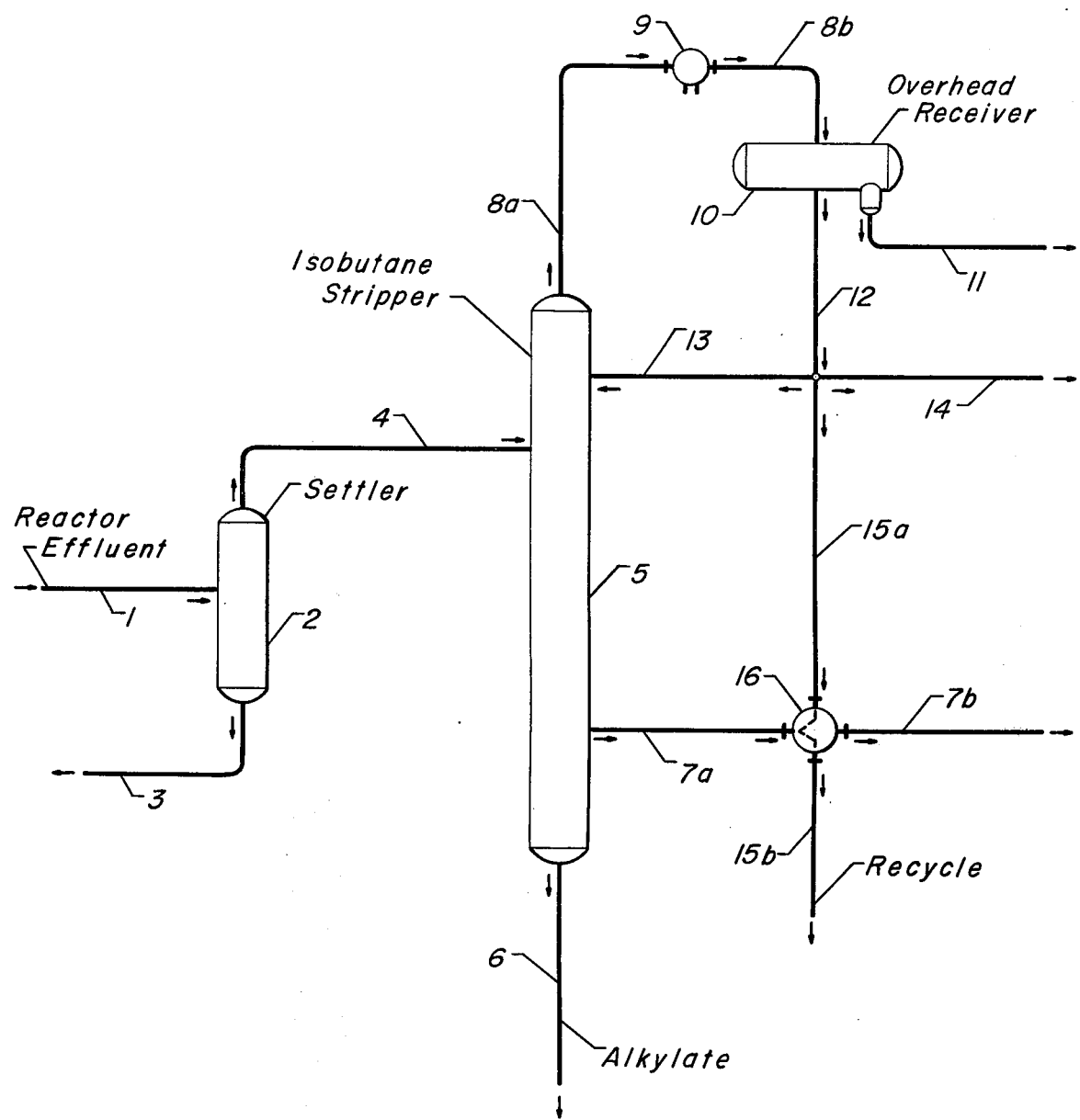

MAINTAINING HF SOLUBILITY IN ALKYLATION ISOBUTANE RECYCLE

BACKGROUND OF THE INVENTION

This invention relates to HF alkylation. Further it relates to the alkylation of an isoparaffin with an olefin. In one aspect, this invention specifically relates to an improved HF alkylation processing scheme in which an isobutane rich recycle stream to an alkylation zone is prepared substantially free of undissolved HF acid.

It is well known in the prior art that catalytic alkylation using hydrofluoric acid or sulfuric acid as the catalyst has become an important chemical tool for preparing alkylated hydrocarbons and derivatives thereof. The commercial and industrial demand for these products is exemplified with the demand for isoparaffin hydrocarbons of gasoline boiling range and with the demand for alkyl-substituted aromatics suitable for conversion to surfactants, e.g., detergents, wetting agents, etc. The prior art process of alkylation generally is effected by contacting an isoparaffin hydrocarbon feedstock with an olefin hydrocarbon in the presence of a catalyst such as hydrofluoric acid in a suitable reaction vessel for conducting chemical reactions.

In practice, there have been numerous process schemes advanced by the prior art for accomplishing the alkylation reaction, but it is extremely difficult to achieve a process scheme which embodies all of the desirable features of a completely optimum reaction. Optimizing the alkylation reaction is complicated by the fact that the alkylation reaction if not carried out properly has many side reactions, such as polymerization, which destroys the effectiveness of the reaction and inhibits the production of commercial quantities of desired alkylate. Additionally, the reaction, in order to be carried out commercially, requires a tremendous amount of auxiliary equipment for the recovery of the alkylate product, for the regeneration and reuse of the excess catalyst, and for the recovery and reuse of the excess reactants which have passed through the reaction zone.

The catalytic alkylation process to which the present invention is applicable consists of a process in which a mixture of hydrocarbons containing isoparaffins such as isobutane, isopentane, and the like, and olefins such as propylene, butenes, isobutenes, and the like, are mixed intimately in the presence of a strong acid catalyst, such as hydrofluoric acid or sulfuric acid, at generally room temperatures or lower for sufficient time to complete the reaction. The effluent from the reaction zone contains saturated isoparaffin hydrocarbons of higher molecular weight or boiling point than the isoparaffin in the original mixture. For convenience, these higher molecular weight isoparaffin hydrocarbons which comprise the reaction product from the alkylation zone are called "alkylate." Isobutane has been used almost exclusively as the reactant isoparaffin because of its reactivity and availability to produce high quality alkylate product. In similar manner, among the olefins, butenes and propylenes have been used satisfactorily. In some cases it is desirable to use solely propylene or butene as the olefin reactant.

As is typical in most commercial chemical plants, the reaction between the isoparaffin hydrocarbon and the olefin hydrocarbon is performed with an excess of reactant isoparaffin in the reaction zone. Accordingly, there is a large excess of the reactant isoparaffin hydrocarbon remaining in the effluent from the reaction zone. In the prior art, the effluent from the reaction zone is settled to form an HF phase and a hydrocarbon phase, at least a portion of the hydrocarbon phase subsequently separated by fractionation into several product and recycle streams. This fractionation normally includes an isobutane stripper, from which several streams are withdrawn, including an overhead product stream, a recycle isobutane stream, a n-butane product stream, and an alkylate product stream. The recycle isobutane stream is passed from the isobutane stripper to the reaction zone to provide the excess isobutane required to produce alkylate of high quality.

It has been found that the quality of the isobutane recycle stream will affect the quality of alkylate produced. While prior art has shown that HF, including dissolved HF, in the isobutane recycle stream is harmful to alkylate quality, it has now been found that only undissolved HF is harmful to alkylate quality.

SUMMARY OF THE INVENTION

Accordingly, it is an object of the present invention to provide an alkylation operation from which an increased octane number alkylate can be obtained. Further it is an object of this invention to provide a better quality recycle isobutane stream to an alkylation zone so that the alkylation reactions achieved will result in a higher octane number of the alkylate product.

In a process for producing an alkylation reaction product by reacting an isobutane reactant stream with an olefin-acting reactant stream in contact with an HF acid catalyst wherein said reactant streams are combined with an acid saturated recycle stream hereinafter defined and are contacted with said HF acid catalyst in a reaction zone at alkylation conditions; a resulting reactor effluent is separated to form a principally acid phase and a principally hydrocarbon phase; at least a portion of said principally hydrocarbon phase is separated to provide a vaporous overhead stream, a vaporous product stream containing principally n-butane, and a liquid alkylation reaction product stream; said vaporous overhead stream is condensed, cooled to a separation temperature, and separated to provide an overhead product stream, a reflux stream, an acid liquid stream, and an acid saturated recycle stream including isobutane and entrained acid; and said acid saturated recycle stream is passed without heating to the reaction zone; the embodiment of the invention is the improvement which comprises heating said acid saturated recycle stream to a temperature sufficient to place in solution said entrained acid prior to combination of said acid saturated recycle stream with said reactant streams.

DESCRIPTION OF THE DRAWING

An understanding of this invention may be aided by reference to the accompanying drawing which represents a schematic flow diagram of an embodiment of the invention. The drawing is not intended to limit the improvement to the embodiment shown, nor is it intended to place a limitation on the scope of this invention. Many variations and modifications of the improvement within the scope of this invention will be obvious to those skilled in the art from the description herein provided.

Alkylation reaction zone effluent via line 1 is introduced into settler 2 and separated into a principally HF liquid phase withdrawn via line 3, and a principally hydrocarbon phase withdrawn via line 4 and introduced into isobutane stripper 5. A liquid alkylation reaction product stream is withdrawn via line 6 and a vaporous n-butane product stream via line 7a is withdrawn from isobutane stripper 5. An overhead vapor stream is withdrawn via line 8a, condensed and cooled to a separation temperature of about 50°–140°F. in condenser 9, introduced into overhead receiver 10 via line 8b, and separated into an HF liquid phase and a hydrocarbon phase. The HF liquid phase is withdrawn from overhead receiver 10 via line 11. The hydrocarbon phase, including a small quantity of unsettled acid, is withdrawn via line 12. A first part of said hydrocarbon phase is passed as a reflux stream via line 13 to the top of isobutane stripper 5. A second part of said hydrocarbon phase is passed via line 14 to further fractionation. And a third part of said hydrocarbon phase is passed as an acid saturated recycle stream including isobutane and entrained acid via line 15a to exchanger 16 wherein the temperature of the acid saturated recycle stream is increased to a temperature 1 to 40°F. higher than the separation temperature. From exchanger 16 the acid saturated recycle stream is passed via line 15b to an alkylation reaction zone. Said vaporous n-butane product stream described hereinabove is the heat medium in exchanger 16, passing to and from exchanger 16 via line 7a and 7b, respectively.

DETAILED DESCRIPTION OF THE INVENTION

Alkylatable reactants suitable for use within the scope of this invention are those which have been utilized in prior art processes for producing an alkylate product. Examples of such compounds include the isoparaffins such as isobutane, isopentane, and isohexane. Isobutane is preferred.

Olefinic reactants suitable for alkylating the above-described alkylatable reactants include mono-olefins, polyolefins, and alkylhalides. The preferred olefinic reactants are the $C_3$–$C_5$ mono-olefins, and mixtures thereof. The $C_3$–$C_5$ preferred olefins may be suitably utilized as they are found in petroleum refinery streams and may be utilized where diluted with gases such as hydrogen, nitrogen, methane, ethane, propane, butane, etc. The butylenes are preferred, and in particular, 2-butene.

The hydrogen fluoride catalyst suitable for use in the present invention is well known to the prior art. Normally, this catalyst comprises essentially anhydrous hydrogen fluoride, i.e., having less than 5% water content by weight. The concentration of hydrogen fluoride in the catalyst is normally higher than about 70% by weight. Alkylation conditions are chosen to minimize side reactions, such as olefin polymerization, cracking, halogen substitution, etc., to maximize the formation of desired alkylate products, and to maintain the reaction mixture of hydrocarbons and catalyst as a liquid phase. Generally, alkylation conditions include a temperature of from about 0°F. to about 200°F. For an isoparaffin-olefin alkylation process, the temperature range is typically from about 50°F. to about 150°F. The pressure of the alkylation zone should be such as to maintain the reaction mixture as a liquid phase, and is generally in the range from about 1 atmosphere to about 50 atmospheres. The contact time for the reaction mixture, defined as the ratio of catalyst volume within the reaction zone to volume rate per minute of reactants charged to the reaction zone, will usually be less than 15 minutes, and preferably less than 10 minutes. The catalyst should be present in the reaction mixture in an amount sufficient to provide a catalyst/reactants volume ratio in the range from about 0.5 to about 10. The alkylatable reactant/olefin-acting reactant mole ratio in the alkylation reaction mixture is maintained at a level within the range from about 1 to about 30 and preferably within the range from about 8 to about 20.

Any sort of alkylation zone known to prior art may suitably be employed to admix and contain the alkylation reaction mixture in the practice of this improved process.

Many schemes are known to one skilled in the art of designing isobutane stripper columns. While the present invention is not limited to specific design of an isobutane stripper, a brief description of a typical design will be useful in the explanation of the present invention.

Hydrocarbons substantially free from a major proportion of HF catalyst are withdrawn from the settler vessel associated with the alkylation reaction zone and introduced into an isobutane stripper. The isobutane stripper operates as a fractionation column and accomplishes a substantial separation between propane, lower boiling isobutane, higher boiling n-butane and alkylation reaction product.

The hydrocarbon feed to the isobutane stripper is introduced into the fractionator at about the tenth tray at a temperature of about 140° to 180°F. A principally n-butane product stream including about 60–95 percent n-butane is withdrawn from the isobutane stripper at about the sixtieth tray at a temperature of about 200°F., and a bottoms alkylate product stream is withdrawn at a temperature of about 360°F. Heat is provided to operate the column by a heater in a bottoms circuit. An overhead vapor stream is withdrawn from the column at a temperature of about 130° to 160°F. and a pressure of about 140 to 200 psig., condensed and cooled to a separation temperature of about 50° to 140°F., preferably about 100° to 120°F., and introduced into an overhead receiver, wherein an HF phase and a hydrocarbon phase containing about 60–95 weight percent isobutane are settled. The hydrocarbon phase, which is saturated with acid, also contains a small amount of unsettled acid, which is entrained when the hydrocarbon phase is withdrawn. The HF phase is withdrawn and passed to the alkylation reaction zone. The hydrocarbon phase is withdrawn, and an aliquot portion is passed to the top of the isobutane stripper as a reflux stream, a second aliquot portion is passed to further fractionation, and a third aliquot portion is passed to the reaction zone as an acid saturated recycle stream including isobutane and entrained acid.

In a commercial alkylation unit in which an acid saturated recycle stream is prepared as described hereinabove as a condensed portion of an isobutane stripper overhead vapor stream and the cooling medium used to condense the overhead vapor stream in water, the temperature of the acid saturated recycle stream is about 100°F. At this temperature the saturation concentration of HF acid in the acid saturated recycle stream is about 0.6 weight percent. Entrained acid content is about 0 to 5 weight percent, and isobutane content is about 60 to 95 weight percent. Upstream of the reaction zone the acid saturated recycle stream is combined with an olefin-acting reactant stream only or a combined olefin-acting reactant and isobutane reactant stream. When the acid saturated recycle stream and the olefin-acting reactant stream are combined and mixed thoroughly upstream of the reaction zone, any free, undissolved acid in the acid saturated recycle stream results in unfavorable reaction between the isobutane and olefin-acting reactant, whereas dissolved acid in the acid saturated recycle stream does not cause unfavorable reaction. Accordingly, in the present invention, the acid saturated recycle stream is heated to a temperature sufficient to place in solution the entrained acid prior to combination of the acid saturated recycle stream with the olefin-acting reactant stream. A temperature increase of about 1° to 40°F. above the separation temperature is sufficient to accomplish this.

It is seen from the following data that dissolved HF in the acid saturated recycle stream is not harmful to the octane number of alkylation reaction product, i.e., alkylate, whereas free HF lowers alkylate octane number. Alkylation reaction conditions are constant, and the acid saturated recycle stream temperature is constant except in the case of 1.5% HF dissolved, in which case the acid saturated recycle stream temperature is increased.

| % HF Dissolved In Recycle | 0 | 0.5 | 1.5 |
|---|---|---|---|
| Alkylate RON | 97.3 | 97.1 | 97.2 |
| Alkylate MON | 95.4 | 94.2 | 94.3 |
| Total % HF (0.5% Dissolved) In Recycle | 1.1 | 1.45 | 2.7 |
| Alkylate RON | 96.8 | 96.6 | 96.5 |
| Alkylate MON | 93.7 | 94.8 | 93.9 |

Therefore, one skilled in the art will endeavor to place in solution all HF in the acid saturated recycle stream. In the present invention it is done by heating an acid saturated recycle stream about 1° to 40°F., preferably about 5° to 10°F., above the temperature of saturation, i.e., the temperature to which the isobutane stripper overhead vapors are cooled. In preferred embodiments, the acid saturated recycle stream is heated by exchanging heat with the n-butane product stream or the alkylation reaction product stream. Other methods may be used to place in solution all HF in the acid saturated recycle stream, such as steam tracing and insulating the acid saturated recycle conduit. While the present invention deals with placing in solution all acid in an acid saturated recycle stream, one skilled in the art will also realize the benefit of additional separation of an acid saturated recycle stream so as to remove entrained acid prior to combining the acid saturated recycle and olefin feed streams. Such additional separation may be accomplished by introducing the acid saturated recycle stream into a settling zone downstream of the isobutane stripper overhead receiver, enlarging the volume of the isobutane stripper overhead receiver, or providing other suitable separation means.

I claim as my invention:

1. In a process for producing an alkylation reaction product by reacting an isobutane reactant stream with an olefin-acting reactant stream in contact with an HF acid catalyst wherein said reactant streams are initially combined with an acid saturated recycle stream, as hereinafter defined, and then contacted with said HF acid catalyst in a reaction zone at alkylation conditions; a resulting reactor effluent is settled to form an acid phase and a hydrocarbon phase; said hydrocarbon phase is separated to provide a vaporous overhead stream, a vaporous product stream containing principally n-butane, and a liquid alkylation reaction product stream; said vaporous overhead stream is condensed, cooled to a separation temperature, and separated to provide an overhead product stream, a reflux stream, an acid liquid stream, and an acid saturated recycle stream including isobutane and entrained acid; and said acid saturated recycle stream is combined with said reactant streams as previously indicated; the improvement which comprises heating said acid saturated recycle stream to a temperature sufficient to place said entrained acid in solution therein prior to said combination of said acid saturated recycle stream with said reactant streams.

2. The improved process of claim 1 wherein said olefin-acting reactant is a mono-olefin containing 3 to 5 carbon atoms per molecule.

3. The improved process of claim 1 wherein said acid saturated recycle stream includes about 60 to 95 percent by volume isobutane.

4. The improved process of claim 1 wherein said acid saturated recycle stream is heated in a heat exchanging zone by said vaporous product stream.

5. The improved process of claim 1 wherein said acid saturated recycle stream is heated in a heat exchanging zone by said liquid alkylation reaction product stream.

6. The improved process of claim 1 wherein said acid saturated recycle stream is heated to a temperature of about 1° to 40°F. higher than said separation temperature.

* * * * *